United States Patent [19]

Holden et al.

[11] 4,200,754
[45] Apr. 29, 1980

[54] METHOD FOR PREPARING 7,8-DICHLORO-1,2,3,4-TETRAHYDROISOQUINOLINE

[75] Inventors: Kenneth G. Holden, Haddonfield, N.J.; Carl D. Perchonock, Philadelphia, Pa.

[73] Assignee: SmithKline Corporation, Philadelphia, Pa.

[21] Appl. No.: 9,551

[22] Filed: Feb. 2, 1979

[51] Int. Cl.$^2$ .............................................. C07D 217/06
[52] U.S. Cl. ..................................... 546/150; 546/141; 260/558 R
[58] Field of Search ........................................ 546/150

[56] References Cited

U.S. PATENT DOCUMENTS 3,939,164  2/1976  Kaiser et al. ........................ 546/150

OTHER PUBLICATIONS

Elderfield, "Heterocyclic Compounds" (1952) vol. 4, pp. 369-672, 392-393.
Birch et al., "Chemical Society Journal", (1974) p. 2185 ff.

Primary Examiner—David Wheeler
Attorney, Agent, or Firm—Joseph A. Marlino; Richard D. Foggio; William H. Edgerton

[57] ABSTRACT

A novel process for preparing 7,8-dichloro-1,2,3,4-tetrahydroisoquinoline by cyclizing N-acetyl-2,3-dichlorobenzylaminoacetaldehyde dimethyl acetal with a Lewis acid, reducing, and hydrolyzing the resulting acylated isoquinoline is disclosed.

4 Claims, No Drawings

METHOD FOR PREPARING 7,8-DICHLORO-1,2,3,4-TETRAHYDROISOQUINOLINE

This invention relates to a novel process for preparing 7,8-dichloro-1,2,3,4-tetrahydroisoquinoline. This compound has been disclosed as an inhibitor of the enzyme phenylethanolamine N-methyltransferase (U.S. Pat. No. 3,939,164).

DESCRIPTION OF THE PRIOR ART

In the above-noted patent, the title compound is described as being prepared by the Pomeranz-Fritsch reaction for isoquinolines, which are then reduced to the corresponding tetrahydroisoquinolines. One of the major disadvantages of the Pomeranz-Fritsch reaction is that cyclization of an imine, in this instance 2,3-dichlorobenzylideneaminoacetaldehyde dimethyl acetyl, is carried out in a hot, strong mineral acid, such as sulfuric acid, at elevated temperature (typically around 160° C.) This reaction requires large quantities of hot sulfuric acid and large quantities of base for the work-up procedure. In addition, a great deal of salts are formed, resulting in a waste disposal problem.

In *J. Chem. Soc.* Perkin I., 2185 (1974), a modification of the Pomeranz-Fritsch isoquinoline synthesis was described in which the benzylideneamino-acetal is reduced to a benzylamino-acetal before cyclization. The success of cyclization appeared to be governed by the reactivity of the benzene ring towards electrophlic attack, the poorest reactions being those in which there was no methoxy substituent para to the position of ring closure. In particular, N-benzyl-N-tosylaminoacetaldehyde dimethylacetals lacking sufficient activating substituents in the benzyl group, for example, those having only hydrogen or the electron withdrawing chlorine moiety did not cyclize at all.

DESCRIPTION OF THE INVENTION

According to the process of this invention, N-acetyl-2,3-dichlorobenzylaminoacetaldehyde dimethyl acetal is cyclized to N-acetyl-7,8-dichloro-1,2-dihydroisoquinoline at room temperature with a Lewis acid such as aluminum chloride as the catalyst in an organic solvent. Preferably the organic solvent is a chlorinated solvent such as, for example, methylene chloride, tetrachloroethylene or dichloroethane. Most advantageously the organic solvent employed is dichloroethane. The dihydroisoquinoline is catalytically reduced to the corresponding tetrahydroisoquinoline, which is then hydrolyzed to 7,8-dichloro-1,2,3,4-tetrahydroisoquinoline. The reaction sequence is represented as follows:

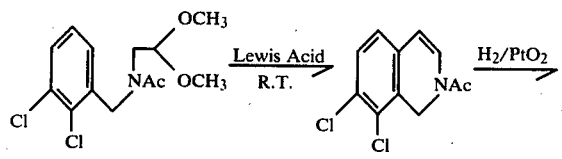

I

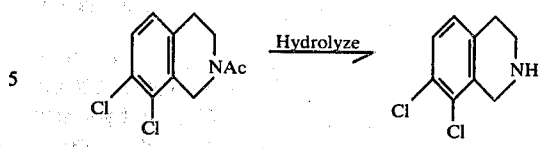

The cyclization step is carried out at room temperature using Lewis acids, such as, for example, aluminum chloride, stannic chloride, titanium chloride and antimony chloride. Most advantageously, the cyclization step is carried out employing aluminum chloride as the catalyst. The 7,8-dichloroisoquinoline is hydrogenated using a hydrogenation catalyst such as platinum oxide.

The above novel process is advantageous in that it is carried out under mild conditions such as room temperature, eliminates the use of hot mineral acids, gives high yields, and affords crystalline products, which facilitates isolation and purification. Where the prior art requires activating substituents in the benzyl group, this invention is particularly effective for non-activating halogen substituents, such as chloro.

The N-acetyl-2,3-dichlorobenzylaminoacetaldehyde dimethyl acetal (I) starting material is prepared by reacting 2,3-dichlorobenzaldehyde with aminoacetaldehyde dimethyl acetal, and the resulting imine, 2,3-dichlorobenzylideneaminoacetaldehyde dimethyl acetal, is catalytically reduced to the corresponding benzylamine. Acetylation of the benzylamine then yields formula (I).

The following example illustrates the process of this invention and the preparation of specific compounds but is not to be construed as a limitation thereof.

EXAMPLE

A mixture of 65.7 g. (0.375 m.) of 2,3-dichlorobenzaldehyde and 39.4 g. (0.375 m.) of aminoacetaldehyde dimethyl acetal was refluxed in 150 ml. of toluene with azeotropic removal of water. The solution was concentrated and the residue distilled to yield 2,3-dichlorobenzylideneaminoacetaldehyde dimethyl acetyl, b.p. 140° C. (0.7 mm).

A solution of 80 g. (0.305 m.) of 2,3-dichlorobenzylidenaminoacetaldehyde dimethyl acetal in 300 ml. of ethyl acetate was divided into two equal parts. Platinum oxide (300 mg.) was added to each and the mixtures were shaken under 20 psi H₂ for about seven hours. Filtration, evaporation, and distillation afforded 2,3-dichlorobenzylaminoacetaldehyde dimethyl acetal, b.p. 100°–125° C. (0.005 mm.).

To a solution of 53.5 g. (0.203 m.) of the above dichlorobenzylaminoacetaldehyde dimethyl acetal in 53.5 ml. (0.664 m.) of pyridine at −10° C. was added 107 ml. (1.13 m.) of acetic anhydride. The volatiles were stripped and the oily residue was seeded and triturated with hexane to yield N-acetyl-2,3-dichlorobenzylaminoacetaldehyde dimethyl acetal as a white solid.

To a suspension of 91 g. (0.682 m.) of aluminum chloride in 1400 ml. of 1,2-dichloroethane was added a solution of N-acetyl-2,3-dichlorobenzylaminoacetaldehyde dimethyl acetal (45.5 g., 0.149 m.) in 230 ml. of 1,2-dichloroethane over an hour, the temperature staying below 30° C. The mixture was then cooled to 0° C. and 1000 ml. of 40% NaOH was added. The mixture was stirred and the layers separated. The aqueous fraction was extracted with 500 ml. of 1,2-dichloroethane and the combined organic layers were washed with 300 ml.

of water and dried over magnesium sulfate. Evaporation and trituration with ether gave 2-acetyl-7,8-dichloro-1,2-dihydroisoquinoline.

A mixture of 5.0 g. (20.7 mm.) of the above dihydroisoquinoline and 90 mg. of platinum oxide in 100 ml. of tetrahydrofuran was shaken under 20 psi of hydrogen for about 3 hours. Filtration, evaporation and trituration with ether yielded 2-acetyl-7,8-dichloro-1,2,3,4-tetrahydroisoquinoline.

The above prepared compound 90 g. (0.369 m.) was added to 2000 ml. of concentrated hydrochloric acid and refluxed for 3 hours. The volatiles were stripped off and the water azeotropically removed with ethanol-toluene. Recrystallization from methanol-ether gave 7,8-dichloro-1,2,3,4-tetrahydroisoquinoline hydrochloride, m.p. 221°–222° C.

What is claimed is:
1. The method of preparing 7,8-dichloro-1,2,3,4-tetrahydroisoquinoline, which comprises the steps of reacting N-acetyl-2,3-dichlorobenzylaminoacetaldehyde dimethyl acetal with a Lewis acid to form N-acetyl 7,8-dichloro-1,2-dihydroisoquinoline, catalytically hydrogenating said dihydroisoquinoline to N-acetyl-7,8-dichloro-1,2,3,4-tetrahydroisoquinoline, and hydrolyzing said tetrahydroisoquinoline to 7,8-dichloro-1,2,3,4-tetrahydroisoquinoline.

2. The method of claim 1 in which the Lewis acid is aluminum chloride.

3. The method of claim 2 in which the reaction is carried out at room temperature.

4. The method of claim 1 in which the hydrogenation catalyst is platinum oxide.